United States Patent [19]
Noller

[11] Patent Number: 5,225,351
[45] Date of Patent: Jul. 6, 1993

[54] REDUCING PHOSPHORESCENT EMISSIONS FROM SUBSTANCES

[75] Inventor: Hans G. Noller, Orange, Calif.

[73] Assignee: Beckman Instruments, Inc., Fullerton, Calif.

[21] Appl. No.: 628,334

[22] Filed: Dec. 17, 1990

[51] Int. Cl.⁵ .................... G01N 1/00; G01N 21/62
[52] U.S. Cl. .................... 436/172; 436/174; 250/361 C
[58] Field of Search ........... 250/484.1 A, 364, 362, 250/361 C, 459.1; 436/172, 164, 165, 166, 172, 174

[56] References Cited

U.S. PATENT DOCUMENTS

| | | | |
|---|---|---|---|
| 2,855,520 | 11/1958 | Stoddart | 250/364 |
| 3,155,451 | 11/1964 | Dunster et al. | |
| 3,208,860 | 10/1965 | Armistead et al. | |
| 3,253,497 | 5/1966 | Dreyer | |
| 3,255,120 | 6/1966 | Cohen | 250/484.1 A |
| 3,355,294 | 11/1967 | Giddings | |
| 3,889,396 | 6/1975 | Aronson | |
| 3,973,966 | 8/1976 | Flannery et al. | |
| 3,982,151 | 9/1976 | Ludovici et al. | |
| 4,028,104 | 6/1977 | Graube | |
| 4,103,996 | 8/1978 | Fergg et al. | |
| 4,150,295 | 4/1979 | Wieder | 250/458.1 |
| 4,205,988 | 6/1980 | Ozaki et al. | |
| 4,275,300 | 6/1981 | Abbott | 250/364 |
| 4,400,619 | 8/1983 | Kotera et al. | |
| 4,507,561 | 3/1985 | Sugita et al. | 250/484.1 A |
| 4,742,226 | 5/1988 | De Filippis | 250/364 |
| 4,778,763 | 10/1988 | Makiguchi et al. | 436/47 |
| 4,818,883 | 4/1989 | Anderson et al. | 250/361 C |
| 4,849,633 | 7/1989 | Yamada et al. | |

OTHER PUBLICATIONS

Bermudez, T. "Counting vial phosphorescence effects in scintillation counting with single photomultiplier" Revista CENIC, Ciencias Fisicas, vol. 5, No. 2, pp. 259-270 (1974).

Primary Examiner—James C. Housel
Assistant Examiner—Jeffrey R. Snay
Attorney, Agent, or Firm—William H. May; Gary T. Hampson; Charles Berman

[57] ABSTRACT

In a method for reducing the latent low-level phosphorescence of laboratory glassware, the glassware is illuminated by infrared light with a wavelength of about 780 nanometers. A suitable infrared light source can be a xenon flash apparatus fitted with an infrared light filter. A single flash from the xenon apparatus can substantially reduce the latent low-level phosphorescence of laboratory glassware to a baseline phosphorescence level.

26 Claims, 1 Drawing Sheet

REDUCING PHOSPHORESCENT EMISSIONS FROM SUBSTANCES

BACKGROUND

Accurate readings for scientific and medical purposes is important. This invention is directed to reducing undesirable phosphorescent radiation from substances so as to enhance accuracy. In particular, the invention is directed to reducing low-level, latent phosphorescence from laboratory glassware.

Many substances possess a latent phosphorescence. Phosphorescence is generally a time-delayed emission of light caused in response to an earlier energy input. Latent phosphorescence is the "memory" in the substance, such as glass, which is due to a past exposure to light, and which is given off as light energy. Latent phosphorescence can interfere with biological assays wherein characteristics of light are measured as part of the detection process.

The problem of latent phosphorescence has been dealt with by keeping containers such as plastic or glass test tubes in dark drawers, or by shielding them with darkened glass. These methods are unsatisfactory because as soon as the laboratory glassware is exposed to laboratory or ambient light, the latent phosphorescence of the glassware begins to rise above a baseline level. Thus, these increased emissions of phosphorescence of the glassware can interfere with luminescent assays such as chemiluminescent, fluorescent or bioluminescent immunological assays.

What is needed, therefore, is a method for reducing the latent phosphorescence of various substances, for instance glassware such as laboratory test tubes.

SUMMARY

The present invention seeks to meet these needs. The method comprises illuminating a substance with light at a predetermined wavelength range, preferably infrared, for a time sufficient to reduce the phosphorescence from the substance.

The light can be sourced selectively from an infrared light generator, an incandescent light source suitably filtered to provide the predetermined wavelength range, a quasi-monochromatic source, or a xenon flash tube. Different selective filtering can be used.

The invention is directed to the method of substance treatment, apparatus for treating the substance, substances so treated, and assays performed with treated substances.

These and other features, aspects and advantages of the present invention are further explained with reference to the following description and the accompanying drawings.

DRAWINGS

DESCRIPTION

Figure 1:
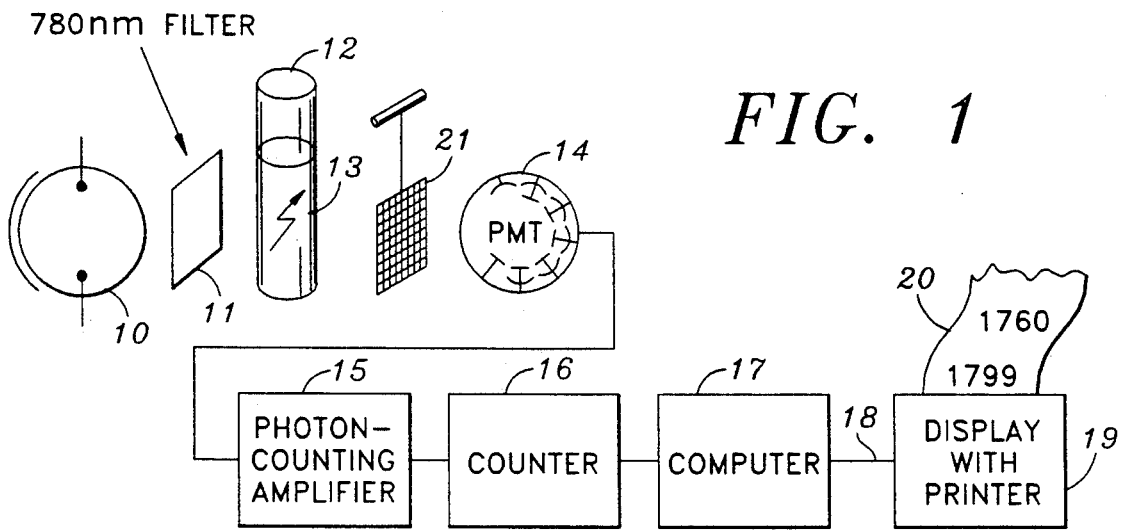
FIG. 1 is a block schematic diagram of a liquid scintillation counter with apparatus for reducing phosphorescent light emission from a substance.

Apparatus for treating vials and performing assays includes a xenon flash 10 in front of which is placed a 780 nm filter. Beyond the filter there is a sample vial or holder 12 in which there is contained sample fluid 13. Also in the vicinity of the vial is a photomultiplier tube 14. The photomultiplier tube 14 detects photons generated from the sample 13 as well as from the vial 12. The tube output is connected with a photon counting amplifier 15. The amplifier 15 is connected with a counter 16 for conditioning the counting signal. A computer with the counter can analyze the spectral results and analyze the data appropriately. The computer 17 can control all other circuitry, motors and all interaction with the user and provide all needed calculations. The computer provides an output 18 to a display 19 with a printer. The output from the display 20 is illustratively shown. Control of the computer 17 can activate the system in any appropriate manner as necessary.

The invented system is directed to removing latent phosphorescence of a substance, particularly in the sample vial 12. This is effected by flashing the vial 12 with the xenon flash 10. The output from the xenon flash is suitably filtered by the filter 11, which is a band-pass filter to permit the wavelength of about 780 nm to pass. With such a flash, latent phosphorescence contained in the vial 12 is reduced to a level not effecting the signal from the sample 13. Essentially, by reducing the signal emanating from the vial 12, the relative noise being detected by the photomultiplier tube 14 of the scintillation counter is reduced relative to the signal of the sample 13 which is activated. In other words, the reduction of the latent phosphorescence provides for the sensing of a relatively higher signal to noise ratio.

The procedure of reducing the phosphorescence emission from a vial, in this case the vial 12, comprises a step of subjecting the substance 12 to illumination at a predetermined wavelength range. The illumination is effected for a sufficient time to reduce the phosphorescence from the vial to a predetermined level. The level is at least a background level for the substance 12 and this is preferably a substantially insignificantly different level relative to the background level.

The illumination is effected preferably by light generated by the xenon flash device 10 and suitably filtered to pass the selected infrared wavelength. One or more flashes of infrared light can be effected on the vial 12. The duration of a xenon flash is in the order of about 0.1 msec. or less; a couple of flashes, for instance ten, can be used for the elimination of the phosphorescence, within a few seconds.

Shutter 21 makes sure that the intensive light from the xenon source does not reach the window of the PMT. The shutter so avoids reduction of the PMT-sensitivity.

Where the substance 12 is glassware such as used in the laboratory, for instance the test tube or vial 12, the level of phosphorescence is reduced effectively. Thus, when activated samples are placed in the glassware 12, the latent phosphorescence of the vial does not effect light characteristic readings of the contents 13.

Infrared light has a wavelength preferably between about 700 nm and about 1,000 nm, and is ideally in a range between about 750 nm and about 850 nm. When the light source is the xenon tube 10, the cutoff or band pass filter 11 of about 800 nm, and preferably 780 nm, is used in conjunction with the tube.

The substance 12 which can be subjected to the light source 10 for the reduction of latent phosphorescence can be the vial 12 and a sample 13 in the vial prior to its being activated into the state to be counted. The illumination bleaches the latent phosphorescence from the substance 12. This is depicted as a lower counts per second (CPS) from the activated vial 13 when an assay or reading of the characteristics of the substance 13 is effected since there is less noise generated relating to the signal.

The illumination can be effected by infrared light for a few seconds. The brighter the infrared light, the shorter will be the necessary time of illumination. In alternative fashion, the light source can be quasi-monochromatic. In this sense, it can be obtained from an infrared light emitting diode (LED) which has a peak of 910 nm. In a different form, any incandescent light source can be used with a filter operative at about 800 nm.

Experimentation has shown that the phosphorescence of the contents of sample 13 tubes prior to activation and also the empty vials 12 themselves need to be controlled carefully to obtain a constant phosphorescence background or baseline reading. The baseline reading can change widely from day to day, from test to test and from batch to batch of DI-water. Trace metal content of the water is a reason for these variations.

Empty vials, namely, standard boro silicate glass tubes, taken from the dark have considerably lower phosphorescence background than those exposed to daylight. For instance, exposing the tubes to a bright light of an unfiltered photo flash (10 flashes) increases the initial phosphorescence 250-fold. This would be represented by 49,000 CPS instead of 200 CPS during the first 20 seconds, logarithmic decay.

Figure 2:
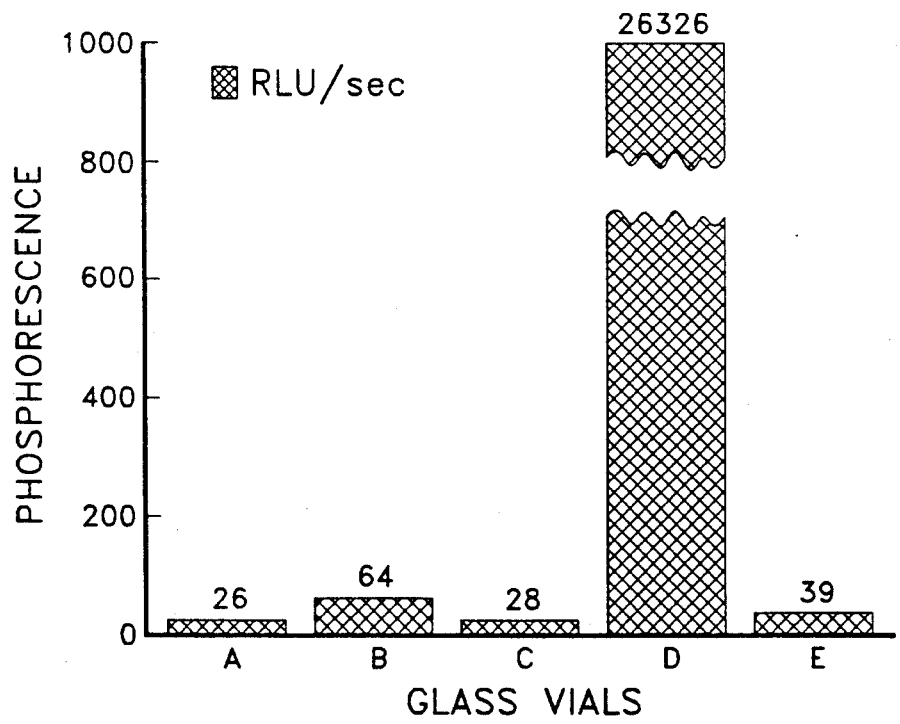
FIG. 2 is a graphical representation demonstrating the various effects on latent phosphorescence in a substance as subjected to different protocols.

In FIG. 2, the effect of bleaching glass vials is illustrated. The five bar graphs illustrate the following:

| | Glass Vials 12 × 75 mm Borosilicate Glass | |
|---|---|---|
| A | taken from the Dark | 26 RLU/s |
| B | exposed for 30 sec. to the ambient lab. light | 64 RLU/s |
| C | vial B after bleaching with 1 xenon-lamp flash 780 nm | 28 RLU/s |
| D | vial A from the Dark after being exposed to 30 flashes from unfiltered xenon-lamp | 26326 RLU/s |
| E | same vial D after bleaching with 10 flashes from xenon-lamp with 780 nm filter | 39 RLU/s |

Accordingly, using a vial of example A, C or E would be highly desirable. The invention is directed to employing bleaching according to examples C or E so that the need of retaining the vial 12 in the dark prior to assay procedures is avoided. The objective is to avoid example B.

EXAMPLE 1

Borosilicate glass tubes used were obtained from Baxter Health Care Corp., Scientific Products Division, McGaw Park, Illinois 60085-6787, as catalog number T1290-3, lot number XB769-60255 73500-55. These are referred to in the catalog as S/P® dis B® culture tubes. The glass test tubes, 12 mm×75 mm in dimension were empty.

In an experiment to illustrate the effects of phosphorescence, a glass vial was located adjacent a xenon flash device 10. The xenon flash lasts for about 1/10,000 of a second. An infrared flash was used to reduce the latent phosphorescence (FIG. 2, Example C). The 30 flashes simulate the effect of a flash tube in an activated system (FIG. 2, Example D). It shows the high variable level of phosphorescence in the substance.

EXAMPLE 2

An experiment was also effected with translucent plastic tubes. The plastic tubes were obtained from American Scientific Products Division of American Hospital Supply Corp., McGaw Park, Illinois 60085, lot number R8P21924, referred to as culture tube/sterile polyprophylene without cap, 12 mm×77 mm, catalog number T1340-103.

Just as with the glass tubes, the plastic tubes were taken from a dark drawer and exposed to xenon flashes before the IR flash to eliminate the latent phosphorescence. Once again, the xenon flashes analogous to FIG. 2, Examples C and E, essentially eliminated the effect of phosphorescence in the substance.

The scintillation counter of FIG. 1 used in Examples 1 and 2 was a Berthold Clinilumat (Prodemate) ® manufactured in Tübing, Germany. The Berthold instrument measures light emissions every 5 seconds as RLU/s, that is, relative light units per second. The baseline of the background is about 20-25 RLU/s.

The xenon flash with the IR filter works best. It is preferred to reduce the latent phosphorescence because only a single flash is required. The xenon flash apparatus can be easily constructed or purchased. Most preferred is one or two flashes from the xenon flash with the IR filter.

Substances from which the latent phosphorescence can be eliminated or at least reduced include glass, inorganic photoluminescent solid phases with organic RTP (room-temperature-phosphorescence) materials, being dry or in solution. They can have dissolved chemiluminescence substances which are used as substrates in immunoassays. These are luminol, lucigenin, bis (2, 4, 6-trichlorphenyl) oxalate.

The most convenient technique for bleaching or removing the latent phosphorescence from a substance such as a vial 12 in the sample 13 prior to adding the activator, such as peroxide, has been found to be a single flash from a potent xenon tube 10. The photo bleaching of the glass vial and the chemiluminescent material and the inorganic and the organic RTP substances by the infrared light of the xenon tube 10 achieves desirable results. The tube 10 is placed in close proximity to the material 12 and the flash from the tube 10 is filtered by an 780 nm cutoff filter 11 to effectively erase the phosphorescence background.

EXAMPLE 3

A test was carried out on a Microtox ™ luminometer. The bleaching phenomenon to remove phosphorescence was also observed in the chemiluminescent area. A luminal-peroxidase-urea peroxide cocktail of standard composition lost about 90% of its emission after a 90-second irradiation with an infrared light source. The light source illuminated the material for 5 seconds and was a low intensity infrared light beam having a wavelength of about 850 nm.

The invention includes a method of bleaching substances and also assay techniques carried out using the substances bleached by the light emissions. These assays can be chemiluminescent, bioluminescent, photoluminescent, phosphorescent, fluorescent or similar immunoassay techniques.

As such, the method of the present invention can be incorporated as part of an assay of radioactive material by scintillation counting. Methods of scintillation counting are well known in the art and are described, for example, in D. Freifelder, "Physical Biochemistry" (2d ed., W.H. Freeman, New York, 1982), ch. 5, "Radioactive Labeling and Counting,"pp. 129-168. The contents of that text are incorporated by reference herein. Briefly, a radioactive sample is placed in suspension or solution in a container together with a luminescent sample such as a fluorescent substance that is capable of converting the electrons emitted by the radioactive sample to pulses of light. These pulses of light are counted to determine the quantity of radioactivity present in the sample. With the invention, the vial 12 and/or sample 13 prior to incorporation of the aotivated oharacteristics, is bleached by the flash as described.

The present invention is believed to operate on the principle that the infrared energy is received by the vial 12 and transmuted into heat energy. This would result in increased molecular vibration which would cause a transmutation of the electron energy which is expressed as phosphorescence into further molecular motion. Accordingly, the infrared flash would likely not cause a further increase in electronic excitation which leads to higher background phosphorescence that may cause probably greater molecular motion through removal of the stored energy in the electrons. Such energy would otherwise be shown as latent phosphorescence. The infrared energy removes inherent stored energy in the substance 12 such as glass or plastic or the inactivated substance 18 which would otherwise emit the energy in the form of phosphorescence, and be generated as noise.

Advantages of the invention include the following. It is no longer necessary to measure the variable background or latent phosphorescence of the substance, such as laboratory glassware before the insertion into the glassware of the activated sample. Thus, there is no need for a subtraction step of that background phosphorescence in order to obtain an accurate evaluation of the activated sample. By automatically removing the latent phosphorescence or maintaining the phosphorescence level at a predetermined standard background value, the procedure for calculating accurately the light characteristics of the anticipated sample is simplified. A standard or preset compensation can be taken for the background level or alternatively the background noise can be essentially eliminated.

Assay results should thus be more accurate since the background phosphorescence can be essentially entirely removed before the beginning of the assay.

With the prior art technique since the background phosphorescence varied according to the environment from which the substance came prior to the addition of activated sample. Results were thus potentially "inaccurate." Also, since the background phosphorescence decays exponentially with time, this actual value of the background phosphorescence at the time of the sample measurement was also time dependent. This then further complicated prior art techniques. The present invention overcomes this difficulty because of the essential removal of all background or latent phosphorescence prior to measuring the activated sample.

Although the present invention has been described in detail with regard to certain preferred embodiments, it is clear that other embodiments within the scope of the present invention are possible. For example, the short exposure to infrared light eliminates reliably the photoexcitation of vials, solutions therein and phosphors.

Many other examples exist each differing from the other in matters of detail only. The scope of the appended claims is not limited to the descriptions of the preferred embodiments. The invention is to be determined by the following claims.

I claim:

1. A method of determining the counts of a sample activated for generating a signal which is selected from the group consisting of chemiluminescence, bioluminescence, and photoluminescence in a holder comprising locating the holder in operative location relative to a sensor, subjecting the holder to illumination at a preselected infrared wavelength range sufficient for reducing latent phosphorescence of the holder, subsequently adding an activated sample to the holder, sensing said signal form the sample, counting the signal so sensed, processing the signal so counted, and displaying the signal so processed as a representation of the activity of the sample.

2. A method as claimed in claim 1 further including the step of determining the quantity of radioactive material present in the sample by scintillation counting.

3. A method as claimed in claim 1 further including the step of using said processed signal for assaying the sample.

4. The method of claim 1 wherein said signal is photoluminescence and comprises phosphorescence, fluorescence or a combination thereof.

5. A method as claimed in claim 1 further including subjecting the holder to illumination at the preselected infraced wavelength range for a sufficient time to reduce latent phosphorescence from the holder to a predetermined level.

6. The method of claim 5 wherein the wavelength of the illumination is between about 700 nm and about 1,000 nm.

7. The method as claimed in claim 5 wherein the holder is glass and the predetermined level of phosphorescence is about that which is characteristic of glass taken from the dark.

8. The method of claim 5 wherein the illumination comprises at least one flash of infrared light.

9. The method of claim 8 wherein the infrared light is generated by a xenon flash device having means for filtering infrared light.

10. The method of claim 5 where the illumination is for a continuous period of less than about 5 seconds.

11. The method of claim 10 wherein the period of continuous illumination is less than about 1 second.

12. The method of claim 11 wherein the period of continuous illumination is less than about 0.1 second.

13. A method of determining the counts of a sample activated for generating a signal which is selected from the group consisting of chemiluminmescence, bioluminescence and photoluminescence in a holder comprising locating the holder in operative location relative to a sensor, adding a substance to the holder, the substance not being activated, subjecting the holder and the substance to illumination at a predetermined infrared wavelength range sufficient for reducing latent phosphorescence of the holder and the substance, subsequently activating the substance to provide an activated sample, sensing said signal from the activated sample, counting the signal so sensed, processing the signal so counted, displaying the signal so processed as a representation of the activity of the activated sample.

14. A method as claimed in claim 13 further including the step of determining the quantity of radioactive material present in the sample by scintillation counting.

15. A method as claimed in claim 13 further including the step of using said processed signal for assaying the sample.

16. The method of claim 13 wherein said signal is photoluminescence and comprises phosphorescence, fluorescence or a combination thereof.

17. A method as claimed in claim 13 further including subjecting the holder to illumination at the predetermined infrared wavelength range for a sufficient time to reduce latent phosphorescence from the holder to a predetermined level.

18. The method of claim 17 wherein the wavelength of the wavelength of the light is between about 700 nm and about 1,000 nm.

19. The method as claimed in claim 17 wherein the holder is glass and the predetermined level of phosphorescence is about that which is characteristic of glass taken from the dark.

20. The method of claim 17 wherein the illumination comprises at least one flash of infrared light.

21. The method of claim 20 wherein the infrared light is generated by a xenon flash device having means for filtering infrared light.

22. The method of claim 17 where the illumination is for a continuous period of less than about 5 seconds.

23. The method of claim 22 wherein the period of continuous illumination is less than about 1 second.

24. The method of claim 23 wherein the period of continuous illumination is less than about 0.1 second.

25. A method of determining in a luminometer the counts of a sample activated for generating a signal which is selected from the group consisting of chemiluminescence, bioluminescence and photoluminescence in a vial comprising locating a borosilicate glass vial in a scintillator counter relative to a sensor, subjecting the vial to illumination at a preselected infrared wavelength range between about 700 nm. and about 1,000 nm. sufficient for reducing phosphorescence of the vial to a level characteristic of glass in the dark, such level being less than about 64 RLU/sec., subsequently adding an activated sample into the vial, sensing said signal from the sample, counting the signal so sensed, processing the signal so counted, and displaying the signal on the counter so processed as a representation of the activity of the sample.

26. The method of claim 25 wherein said signal is photoluminescence and comprises phosphorescence, fluorescence or a combination thereof.

* * * * *